US00PP30144P3

(12) United States Plant Patent
Francis

(10) Patent No.: US PP30,144 P3
(45) Date of Patent: Jan. 29, 2019

(54) APPLE TREE NAMED 'PE'

(50) Latin Name: *Malus domestica*
Varietal Denomination: PE

(71) Applicant: Brendon Francis, Grove (AU)

(72) Inventor: Brendon Francis, Grove (AU)

(73) Assignee: Fruit Varieties International Pty Ltd, Grove, Tasmania (AU)

( * ) Notice: Subject to any disclaimer, the term of this patent is extended or adjusted under 35 U.S.C. 154(b) by 0 days.

(21) Appl. No.: 15/731,671

(22) Filed: Jul. 15, 2017

(65) Prior Publication Data

US 2018/0020583 P1 Jan. 18, 2018

Related U.S. Application Data

(60) Provisional application No. 62/602,361, filed on Apr. 20, 2017.

(30) Foreign Application Priority Data

Jul. 18, 2016 (AU) ..... 2016/189

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
See application file for complete search history.

(56) References Cited

U.S. PATENT DOCUMENTS

| | | | |
|---|---|---|---|
| PP7,880 | P | 6/1992 | Cripps |
| PP16,725 | P2 | 6/2006 | Staples et al. |
| PP18,660 | P2 | 3/2008 | Tuite |
| PP21,606 | P3 | 1/2011 | Barnsby |
| PP27,187 | P3 | 9/2016 | Francis |

*Primary Examiner* — Annette H Para
(74) *Attorney, Agent, or Firm* — Phase M Legal

(57) ABSTRACT

A new and distinct apple tree (*Malus domestica*) named 'PE'. 'PE' is a spontaneous limb mutation of 'Cripps Pink' and is distinguished by its very early full pink-red color over the entire fruit surface, even in shaded areas of the limb. 'PE' is also distinguished from its parent by its early maturity, reddish-brown wood color on the sunny side, very large level of leaf anthocyanin, high levels of young fruit anthocyanin, and high intensity of Pink-Red overcolor. The pattern of overcolor is solid blush. Leaf blade incisions are serrate type 1, there are fewer lenticels on one-year-old wood, and leaf blade length and width are also smaller than for the parent.

9 Drawing Sheets

Latin name of the genus and species: Botanical classification: *Malus domestica.*

Variety denomination: The new apple tree variety denomination is 'PE'.

BACKGROUND OF THE VARIETY

The present invention is a new and distinct cultivar of apple tree botanically known as *Malus domestica* and referred to by the cultivar name 'PE'. 'PE' was discovered as a spontaneous limb mutation of an eleven-year old 'Cripps Pink' tree in an orchard planting of the variety 'Cripps Pink' (U.S. Plant Pat. No. 7,880 expired) in Tasmania, Australia.

'PE' was first observed on Feb. 21, 2013 in Dover, Tasmania, Australia, where it was distinguished by very early full pink-red color over the entire fruit surface, even in shaded areas of the limb. 'PE' is also distinguished from its parent by its early maturity, reddish-brown wood color on the sunny side, very large levels of leaf anthocyanin, high levels of young fruit anthocyanin, and high intensity of pink-red overcolor. The pattern of overcolor is solid blush. Leaf blade incisions are serrate type 1, there are fewer lenticels on one-year-old wood and leaf blade length and width are also smaller than for the parent 'Cripps Pink'.

Asexual reproduction of 'PE' was carried out by bud grafting in 2013 and trees of 'PE' were planted for additional observation at Lucaston, Tasmania, Australia. 'PE' has since been fruited through 3 successive asexually propagated generations at Lucaston, Tasmania, Australia and has been observed to remain true to type with the distinguishing characteristics retained through successive generations of asexual reproduction.

BRIEF DESCRIPTION OF THE VARIETY

The new variety 'PE' claimed herein is primarily distinguished by its very early full pink-red color over the entire fruit surface, even in shaded areas and its early maturity. These and other distinguishing characteristics are set forth in the tables below. Under similar growing conditions in Tasmania, Australia, under commercial practice, 'PE' is distinguishable from its parent 'Cripps Pink' as described in Table 1 below:

TABLE 1

Comparison of 'PE' to 'Cripps Pink'

| Characteristic | 'Cripps Pink' | 'PE' |
|---|---|---|
| One-year-old shoot on Sunny Side | Light-Brown | Reddish-Brown |
| Petiole Anthocyanin | Small | Very Large |
| Young Fruit Anthocyanin | Absent/Small | Medium |
| Fruit - Area of Overcolor | Small | Very Large |
| Fruit - Intensity of Overcolor | Light | Dark |
| Fruit - Pattern of Overcolor | Weak Stripes with Solid Flush | Solid Flush Only |
| Fruit - Time for Harvest | Very Late | Late |
| Fruit - Time for Eating | Very Late | Late |
| Leaf Blade - Incisions of Margin Upper Half | Bi-Crenate | Serrate Type 1 |
| One-Year-Old Shoot - Number of Lenticels | 140 average per 100 mm of stem - Many | 97 average per 100 mm of stem - Medium |
| Leaf Blade - Width | 71 mm average | 61 mm average |
| Leaf Blade - Length | 103 mm average | 85 mm average |

A comparison of 'PE' to 'PLBAR B1' (U.S. Plant Pat. No. 21,606), 'Ruby Pink' (U.S. Plant Pat. No. 16,725), and 'Lady in Red' (U.S. Plant Pat. No. 18,660), the most similar varieties of common knowledge, are set forth in Table 2a, 2b and 2c below:

TABLE 2a

Comparison of 'PE' to 'Lady in Red' (U.S. Plant Pat. No. 18,660)

| Characteristic | 'Lady in Red' (U.S. Plant Pat. No. 18,606) | 'PE' |
|---|---|---|
| One-Year-Old Shoot - Color on Sunnyside | Light Brown to Medium Brown | Reddish Brown |
| Petiole - Anthocyanin | Small | Very Large |
| Young Fruit - Extent of Anthocyanin Overcolor | Absent to Very Small | Large |
| Fruit - Relative Area of Overcolor | Small | Very Large |
| Fruit - Intensity of Overcolor | Light | Dark |
| Fruit - Pattern of Overcolor | Weak Stripes with Solid Flush | Only Solid Flush |
| One-Year-Old Shoot - Number of Lenticels | 140 average lenticels per 100 mm shoot | 97 average lenticels per 100 mm shoot |
| Leaf - Length | 95 mm average length | 85 mm average length |
| Leaf - Width | 65 mm average width | 60 mm average width |
| Time for Harvest | Very Late | Late |
| Time for Eating | Very Late | Late |
| Leaf Blade - Incisions of Margin - Upper Half | Bi-Crenate | Serrate type 1 |

TABLE 2b

Comparison of 'PE' to 'Ruby Pink' (U.S. Plant Pat. No. 16,725)

| Characteristic | 'Ruby Pink' (U.S. Plant Pat. No. 16,725) | 'PE' |
|---|---|---|
| One-Year-Old Shoot - Color on Sunnyside | Light Brown to Medium Brown | Reddish Brown |
| Petiole - Anthocyanin | Small | Very Large |
| Young Fruit - Extent of Anthocyanin Overcolor | Absent to Very Small | Large |
| Fruit - Relative Area of Overcolor | Small | Very Large |
| Fruit - Intensity of Overcolor | Light | Dark |
| Fruit - Pattern of Overcolor | Weak Stripes with Solid Flush | Only Solid Flush |

TABLE 2b-continued

Comparison of 'PE' to 'Ruby Pink' (U.S. Plant Pat. No. 16,725)

| Characteristic | 'Ruby Pink' (U.S. Plant Pat. No. 16,725) | 'PE' |
|---|---|---|
| Time for Harvest | Very Late | Late |
| Time for Eating | Very Late | Late |
| Leaf Blade - Incisions of Margin - Upper Half | Bi-Crenate | Serrate type 1 |

TABLE 2c

Comparison of 'PE' to 'PLBAR B1' (U.S. Plant Pat. No. 21,606)

| Characteristic | 'PLBAR B1' (U.S Plant Pat. No. 21,606) | 'PE' |
|---|---|---|
| One-Year-Old Shoot - Color on Sunnyside | Light Brown to Medium Brown | Reddish Brown |
| Petiole - Anthocyanin | Small | Very Large |
| Young Fruit - Extent of Anthocyanin Overcolor | Absent to Very Small | Large |
| Fruit - Relative Area of Overcolor | Small | Very Large |
| Fruit - Intensity of Overcolor | Light | Dark |
| Fruit - Pattern of Overcolor | Weak Stripes with Solid Flush | Only Solid Flush |
| One-Year-Old Shoot - Number of Lenticels | 140 average lenticels per 100 mm shoot | 97 average lenticels per 100 mm shoot |
| Leaf - Length | 95 mm average length | 85 mm average length |
| Leaf - Width | 65 mm average width | 60 mm average width |
| Leaf Blade - Incisions of Margin - Upper Half | Bi-Crenate | Serrate type 1 |

BRIEF DESCRIPTION OF THE PHOTOGRAPHS

Typical specimens of the tree and blossoms for the new apple tree variety 'PE' from a four-year old tree grown on MM106 rootstock are shown in the accompanying photographs in comparison to specimens of known tree varieties of comparable age also grown on MM106 rootstock. The colors shown are as true as possible within the usual limits of this kind of illustration.

DETAILED BOTANICAL DESCRIPTION OF THE VARIETY

Figure 1:
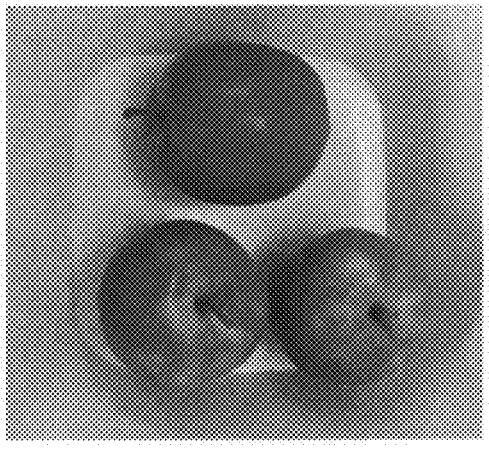
FIG. 1 illustrates the distinctive color of fresh fruit of 'PE' harvested at maturity as compared to immature fruit of 'Cripps Pink' and 'Ruby Pink' of comparable age and growth.
Figure 1:
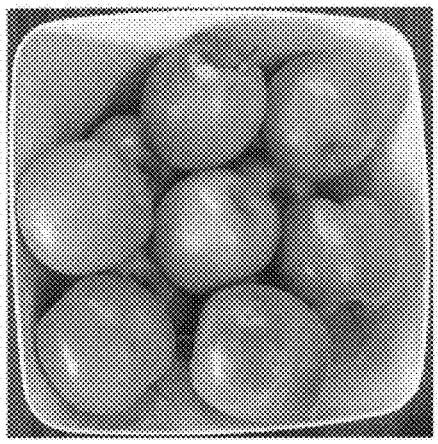
Figure 1:
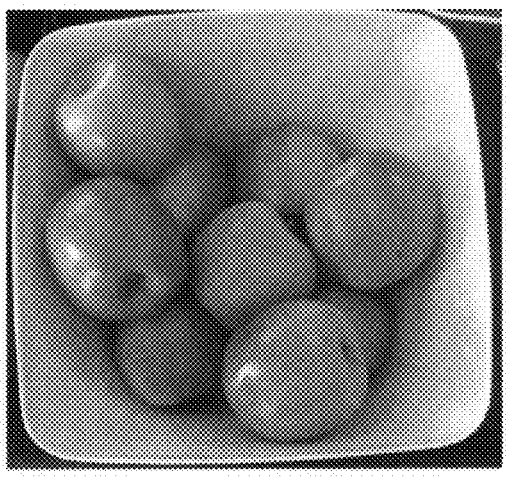
Figure 2:
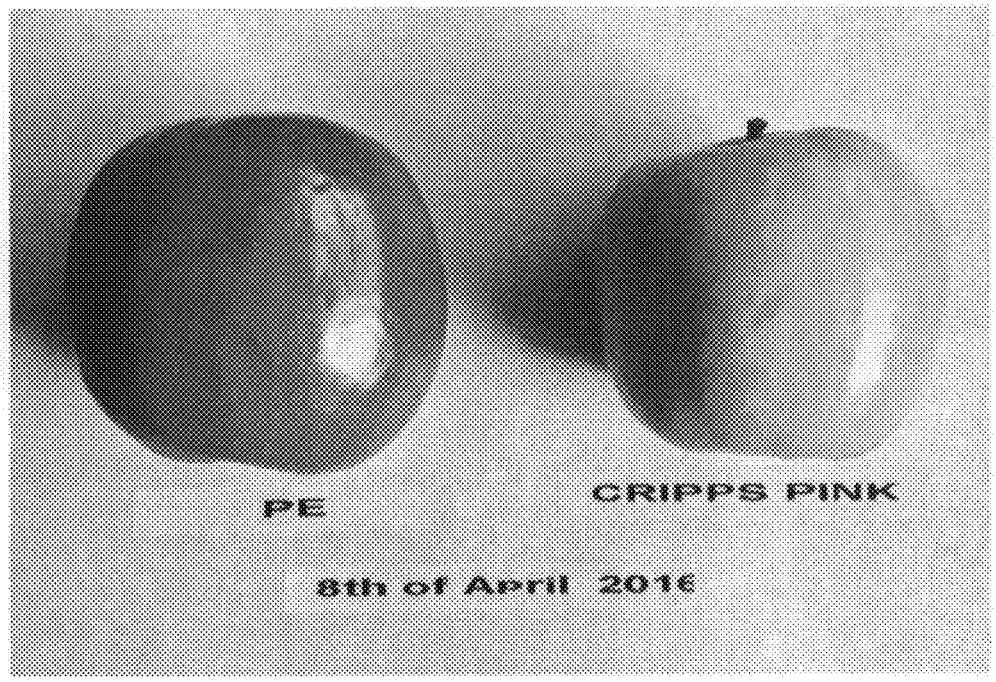
FIGS. 2 and 3 show an apple of 'PE' illustrating its distinctive color and advanced maturity in comparison to an apple of 'Cripps Pink' of the same age and growing conditions.
Figure 3:
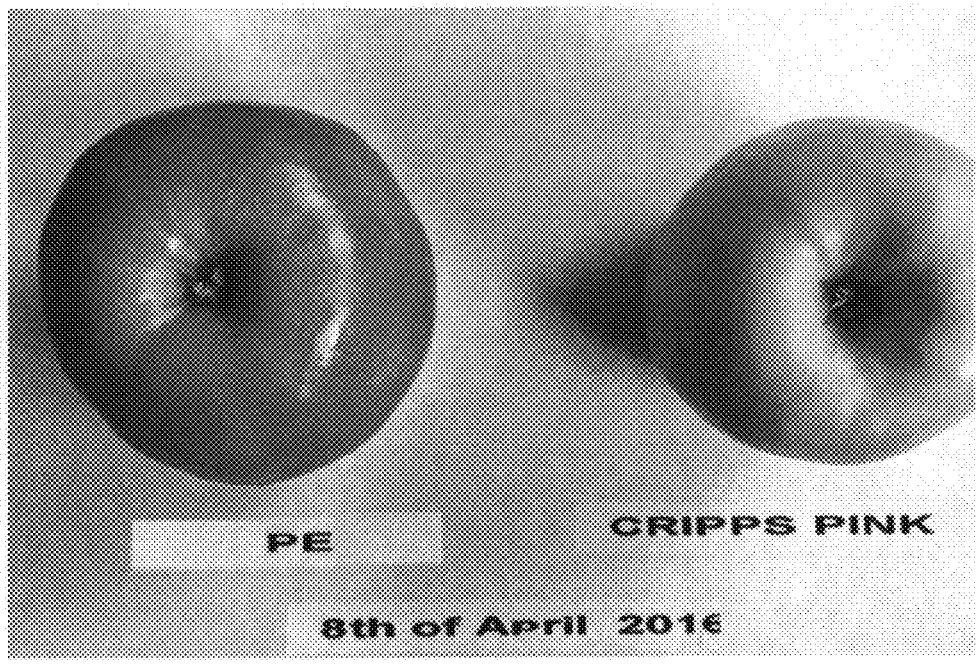
Figure 4:
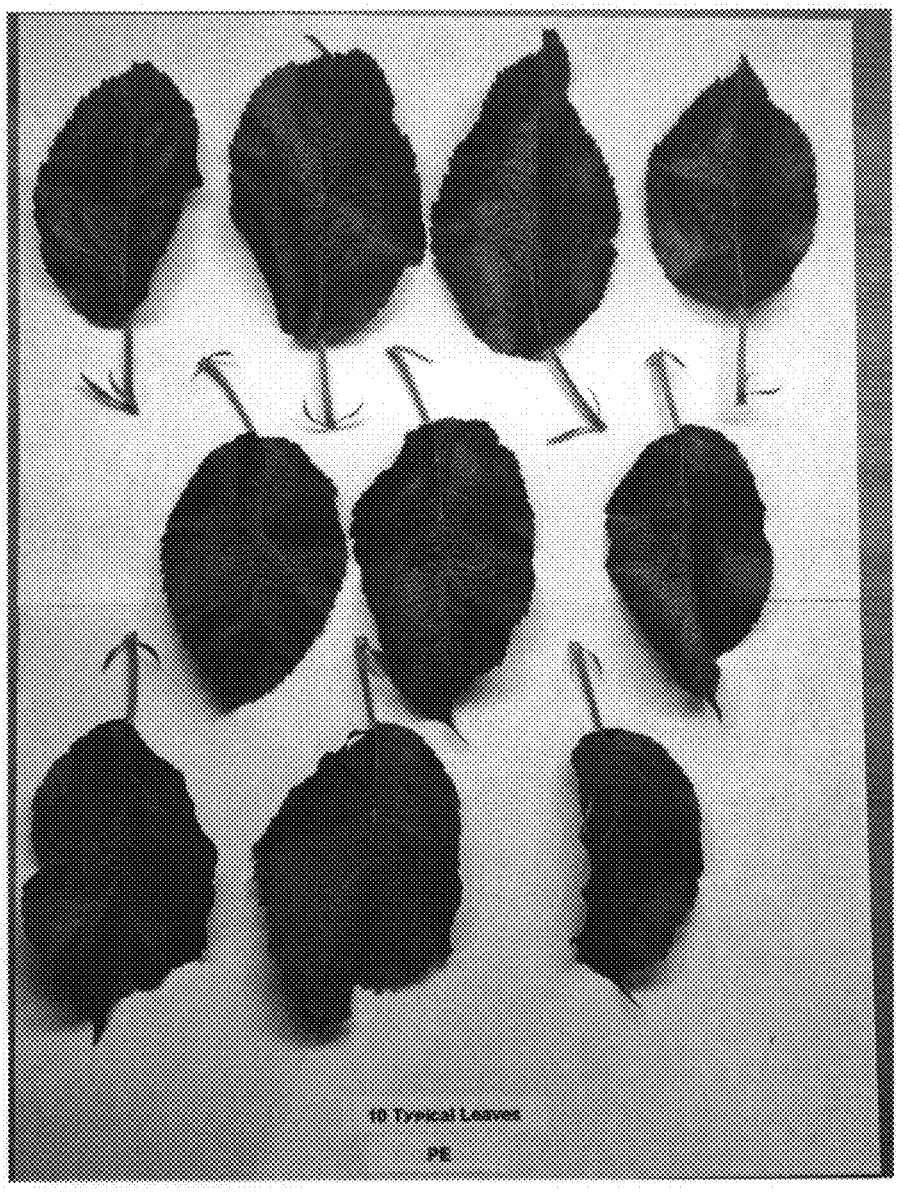
FIG. 4 shows an upper side view of leaves of 'PE'.
Figure 5:
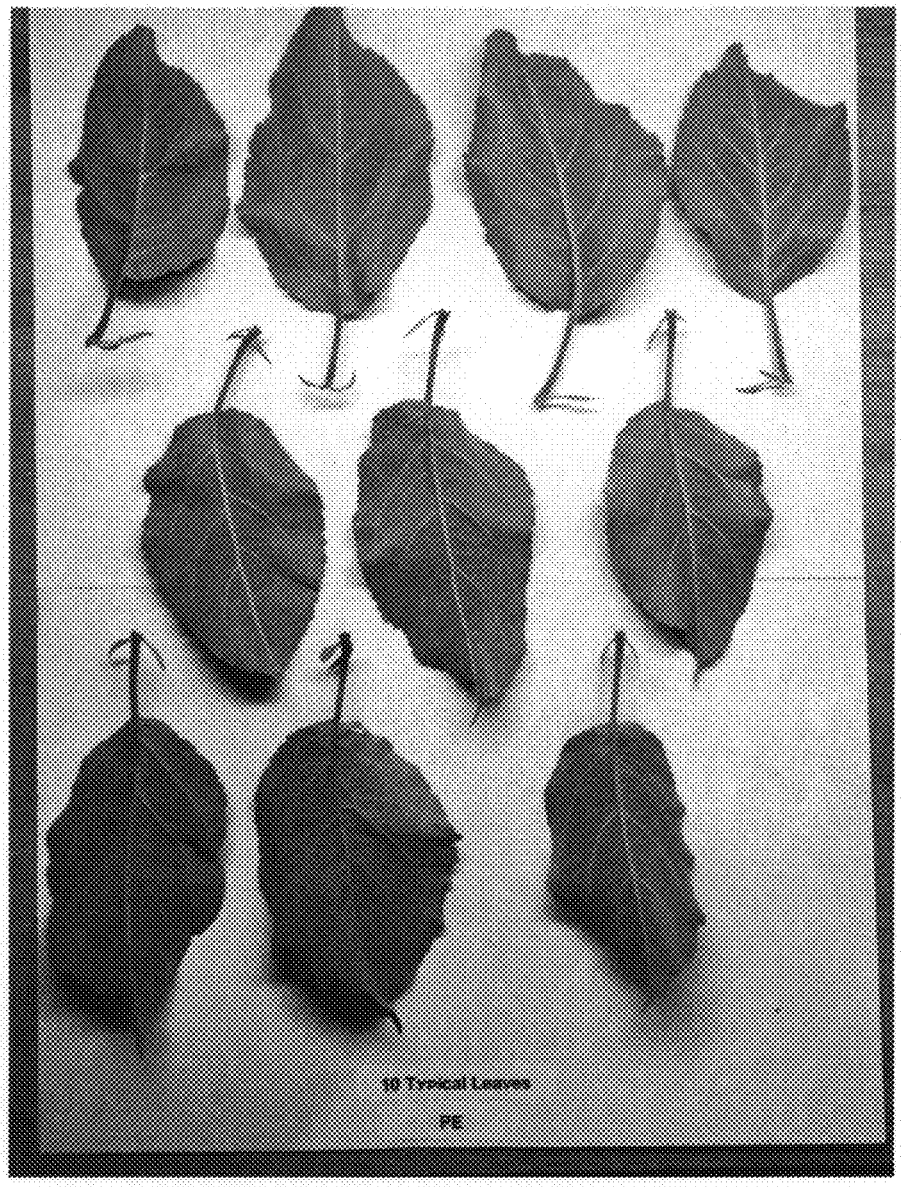
FIG. 5 shows an underside view of leaves of 'PE'.
Figure 6:
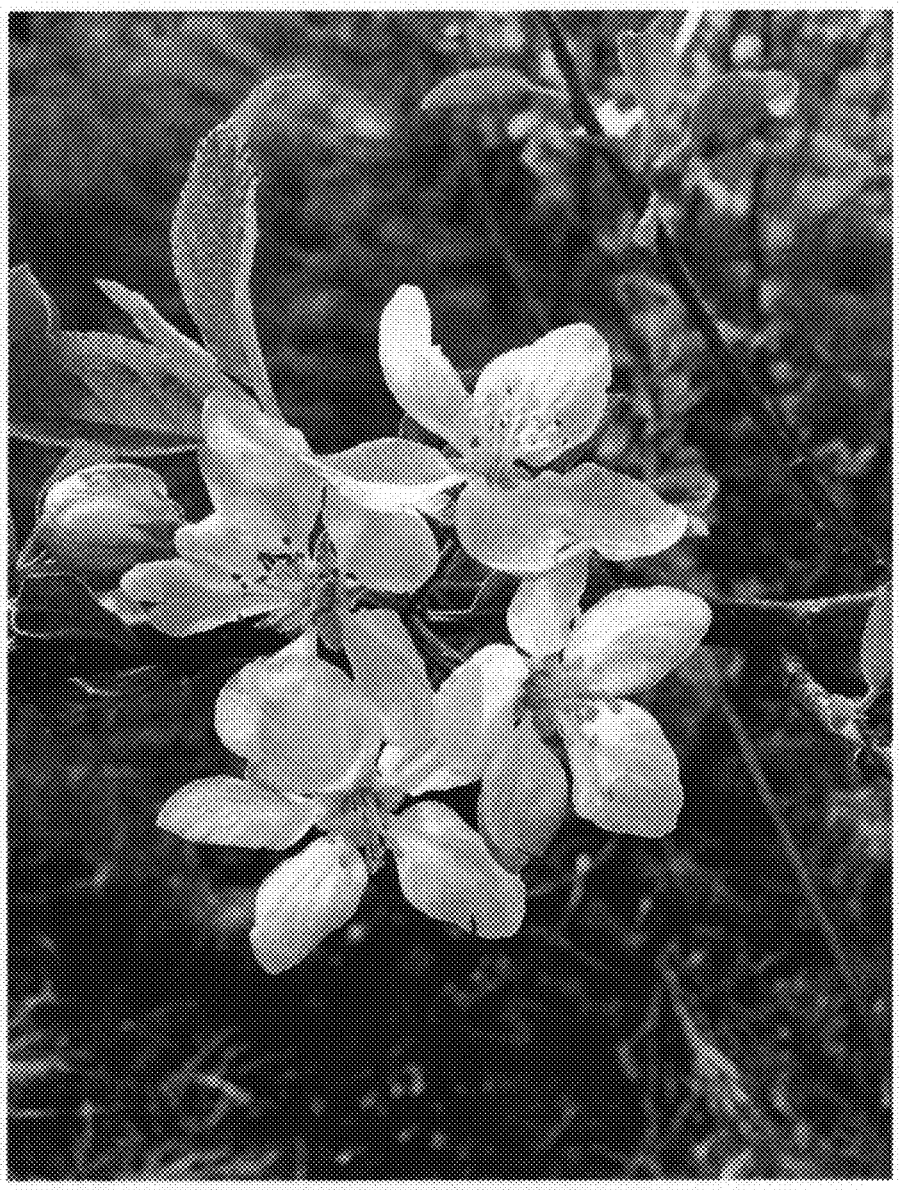
FIG. 6 shows a cluster of flowers of 'PE' on a 'PE' tree.
Figure 7:
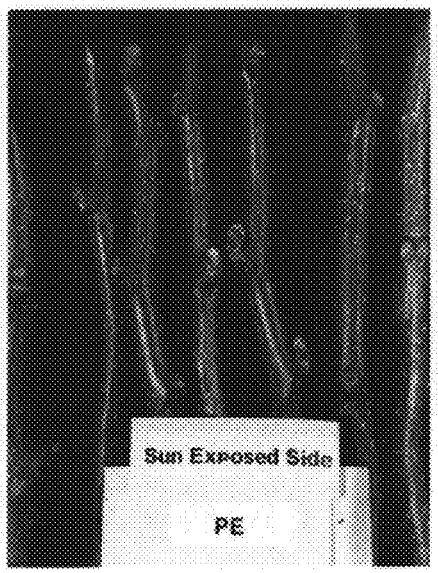
FIG. 7 shows the sun exposed side of the wood of a 'PE' tree illustrating its distinctive color in comparison to 'Ruby Pink'.
Figure 7:
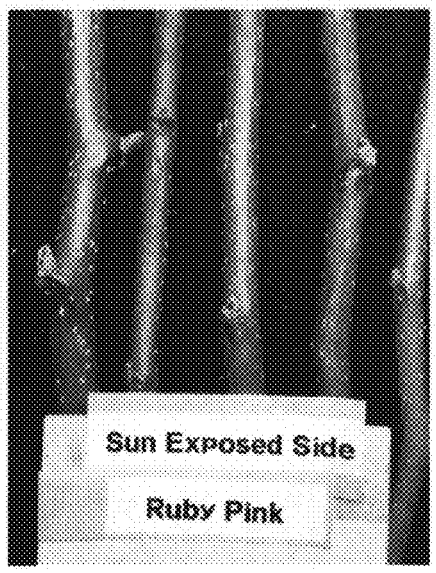
Figure 8:
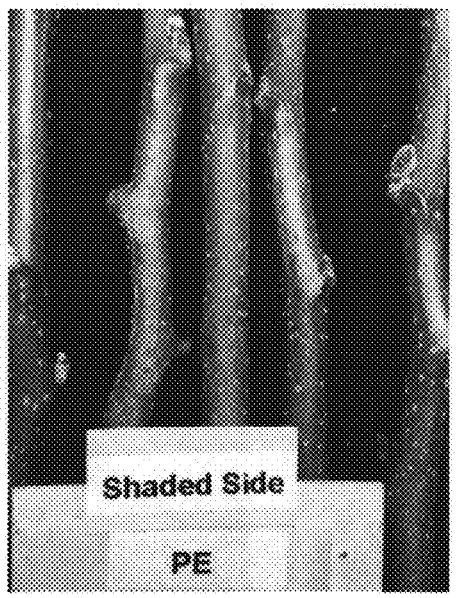
FIG. 8 shows the shaded side of the wood of a 'PE' tree in comparison to 'Ruby Pink'.
Figure 8:
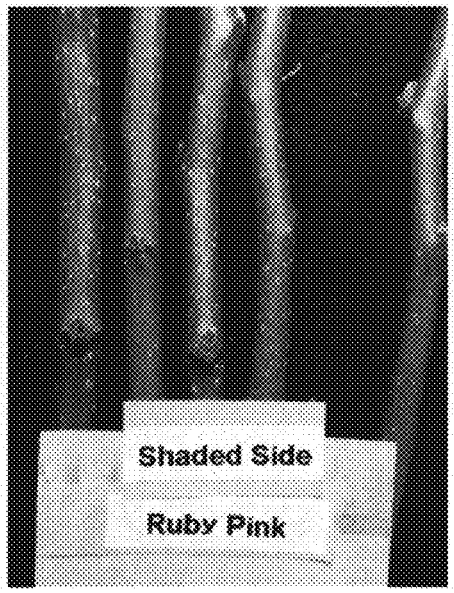
Figure 9:
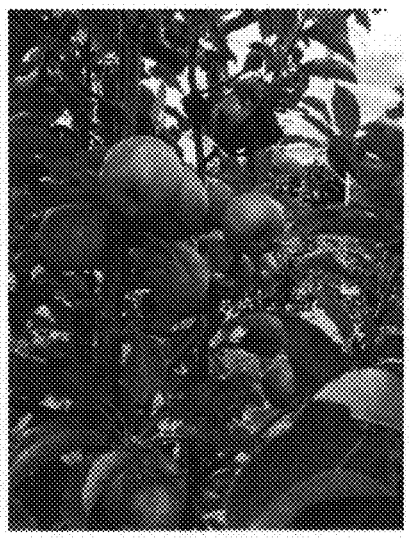
FIG. 9 shows 'PE' fruit on the tree illustrating its distinctive color and maturity in comparison to fruit of the same age and comparable growing conditions for 'Cripps Pink', 'Lady in Red' and 'Ruby Pink'.
Figure 9:
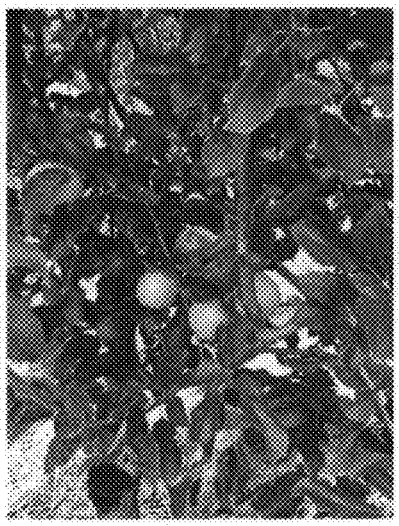
Figure 9:
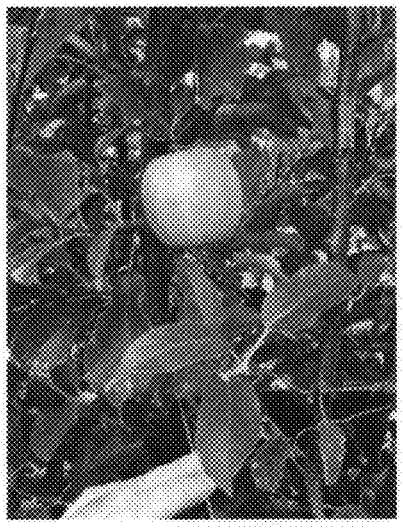
Figure 9:
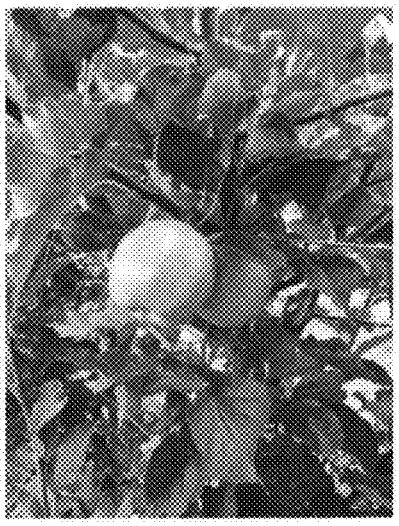

The following-detailed botanical description is based on observations made during the 2016 and 2017 growing season at Lucaston, Tasmania, Australia of three-year old trees planted on MM106 rootstock (unpatented). The cultivar has not been observed under all possible environmental conditions. The phenotype may vary significantly with variations in the environment such as temperature, length of day and light intensity, without any variance in genotype. It should be understood that the characteristics described will vary somewhat depending upon cultural practices and climatic conditions, and will vary with location and season. The plant and flower quantified measurements and foliage size are expressed as an average of measurements taken from a number of individual plants of the PE using standard commercial cultural practices. The measurements of any individual plant or any group of plants of the 'PE' may vary from the stated average. All colors are described according to The Royal Horticultural Society Colour Chart ($5^{TH}$ edition 2007).

Tree:

*Vigor.*—Medium to Strong.

*Trunk cross sectional area.*—6.75 $cm^2$ — average of 10 four-year old trees grown on MM106 rootstock.

*Average seasonal growth.*—785 mm per year — average of 10 four-year old trees grown on MM106 rootstock.

*Type.*—Ramified, bearing on spurs and long shoots.

*Habit.*—Spreading to occasionally upright.

*Height.*—2.51 m.

*Trunk diameter.*—47 mm.

*Bark texture.*—Smooth with some ridging.

*Bark color.*—Greyed-Brown N199A on sun exposed side And Greyed-Brown N199A on shaded side.

*Branch.*—Fruiting branches located at around 700 mm Above the graft union.

*Length.*—1.9 m average.

*Diameter.*—27.5 mm average at base.

*Crotch angle.*—Branches on unpruned tree are spreading To upright from horizontal to 30 degrees In angle.

*Bark color.*—Greyed-Brown N199A on sun exposed side And Greyed-Brown N199A on shaded side.

*Lenticel length.*—1.25 mm on average.

*Lenticel color.*—Greyed-Orange 164B.

*Quantity of lenticels per $cm^2$.*—4 to 6.

One-year old shoot:

*Length.*—700 mm average.

*Color.*—Greyed-Purple 183B on sun exposed side and Yellow-Green 152A on shaded side.

*Pubescence.*—Very Weak to Weak.

*Thickness.*—6.81 mm.

*Internode length.*—35 mm.

*Number of lenticels per $cm^2$.*—4 to 6 range — average of 97 per 100 mm section.

Flowers:

*Diameter of fully open flower.*—51.32 mm.

*Relative position of petal margin.*—Free to touching.

*Quantity of flowers per cluster.*—5 to 7 range.

*Date of beginning of flowering.*—5 Oct. 2016 in Tasmania.

*Date of full bloom.*—20 Oct. 2016 in Tasmania.

*Pollination requirement.*—Pollination required by another diploid variety flowering at similar time.

Petals:

*Quantity per flower.*—5 petals per flower.

*Shape.*—Ovate to Ellipsoid.

*Length.*—22.9 mm.

*Width.*—15.5 mm.

*Apex.*—Ovoid to Elliptic.

*Base.*—Cuneate to Obovate at base.

*Margin.*—Smooth.

*Color.*—Upper surface — White in Color NN155C.

*Color.*—Lower surface — Red-Purple in Color 61B.

*Pistils.*—15.9 mm long; Yellow-Green Color 150C.

*Stigma.*—1.15 mm diameter; Yellow-Green Color 152A.

*Position of stigma relative to anther.*—Occasionally above, mostly the same level.

*Style.*—5; Fused and Pubescent at the base; Length 8.06 mm; Color: Yellow-Green 150C.

*Ovary.*—Pubescent; 2.71 mm diameter; Color Yellow-Green 150C.

*Anthers.*—18 to 20 per flower; Length 2.73 mm; Width 1.93 mm; Ample pollen, Color Yellow 6D.

*Pedicel.*—Length 36.25 mm; Diameter 1.98 mm; Color: Red-Purple 59A on sun exposed side; Color Yellow-Green 144B on shaded side.

*Sepals.*—Quantity 5; Length 9.07 mm; Color: Yellow-green 144B with Red-Purple 59A on tip; Recurved shape with smooth straight margin; Very Pubescent.

Leaves:

*Length.*—85 mm.

*Width.*—60 mm.

*Length/width ratio.*—5.6:4.

*Blade margin.*—Serrate Type 1.

*Shape.*—Oval to Obtuse.

*Apex.*—Shape: Mostly Acute to occasionally Elliptic.

*Base.*—Shape: Obovate to Obtuse in shape.

*Pubescence.*—Lightly Pubescent on underside.

*Color.*—Upper surface — Green 137A.

*Color.*—Lower surface — Yellow-Green 147C.

*Attitude in relation to shoot.*—Outward.

*Petiole.*—Length 26.8 mm; Diameter 26.80 mm; Color: Very High Level of Anthocyanin starting at base of petiole and extending well into leaf blade. Typically colored Red-Purple 59B extends 32.1 mm in length along petiole.

Fruit:

*Quantity per cluster.*—5 to 7 per cluster if no thinning occurs.

*General shape in profile.*—Cylindrical and slightly Ellipsoid at base.

*Position of maximum diameter.*—Near center.

*Ribbing.*—Moderate.

*Crowning at calyx end.*—Moderate.

*Amount of overcolor.*—Very High 95% to 100% on all fruit.

*Intensity of overcolor.*—Dark.

*Pattern of overcolor.*—Solid flush.

*Amount of russet around stalk cavity.*—Low to medium.

*Amount of russet on cheeks.*—Absent.

*Area of russet around eye basin.*—Absent.

*Seeds.*—Minimum of 1, mostly 2 per cell; 9 per fruit. Acute in shape; Greyed-orange 167B. Aperture of locules closed or slightly open.

*Fruit size.*—Average to large.

*Observed fruit weight.*—196 g — average of ten typical fruit of four-year old trees.

*Percent soluble solids.*—15% — average of ten typical fruit of four-year old trees.

*Titratable acidity.*—0.6% — average of ten typical fruit of four-year old trees.

*Penetrometer reading.*—8.8 kg — average of ten typical fruit of four-year old trees.

*Disease/insect resistance/susceptibility.*—No resistance/susceptibility noted.

*Market use.*—Fresh.

I claim:

1. A new and distinct apple tree substantially as described and illustrated herein.

* * * * *

'PE'

'CRIPPS PINK'

'RUBY PINK'

'PE'

'Cripps Pink'

'Lady in Red'

'Ruby Pink'